United States Patent
Andersson et al.

(10) Patent No.: US 9,642,754 B2
(45) Date of Patent: May 9, 2017

(54) ABSORBENT ARTICLE HAVING ACQUISITION LAYER

(71) Applicant: SCA Hygiene Products AB, Göteborg (SE)

(72) Inventors: Patrik Andersson, Göteborg (SE); Louise Grahn, Göteborg (SE); Shabira Abbas, Göteborg (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 15/037,431

(22) PCT Filed: Dec. 3, 2013

(86) PCT No.: PCT/SE2013/051432
§ 371 (c)(1),
(2) Date: May 18, 2016

(87) PCT Pub. No.: WO2015/084221
PCT Pub. Date: Jun. 11, 2015

(65) Prior Publication Data
US 2016/0287450 A1 Oct. 6, 2016

(51) Int. Cl.
*A61F 13/15* (2006.01)
*A61F 13/20* (2006.01)
(Continued)

(52) U.S. Cl.
CPC .. *A61F 13/51121* (2013.01); *A61F 13/15203* (2013.01); *A61F 13/49014* (2013.01);
(Continued)

(58) Field of Classification Search
CPC .............. A61F 13/512; A61F 13/5126; A61F 13/53747; A61F 13/5376; A61F 2013/5127; A61F 2013/5128; A61F 2013/53782
See application file for complete search history.

(56) References Cited

U.S. PATENT DOCUMENTS 5,728,081 A * 3/1998 Baer ................. A61F 13/53747
604/367
6,348,253 B1 2/2002 Daley et al.
(Continued)

FOREIGN PATENT DOCUMENTS

| EP | 2 353 562 A1 | 8/2011 |
|---|---|---|
| WO | WO 00/59431 A1 | 10/2000 |
| WO | WO 2005/115294 A2 | 12/2005 |
| WO | WO 2007/035038 A1 | 3/2007 |
| WO | WO 2013/002686 A1 | 1/2013 |

OTHER PUBLICATIONS

International Search Report (PCT/ISA/210) issued on Aug. 14, 2014, by the Swedish Patent Office as the International Searching Authority for International Application No. PCT/SE2013/051432.
(Continued)

*Primary Examiner* — Michele M Kidwell
(74) *Attorney, Agent, or Firm* — Buchanan Ingersoll & Rooney PC

(57) ABSTRACT

An absorbent article includes a liquid permeable top sheet, a liquid impermeable back sheet, an absorbent core being arranged between the top sheet and the back sheet, and an acquisition and distribution layer (ADL) of a nonwoven material being arranged between the top sheet and the absorbent core. The nonwoven material has a basis weight of 20-40 g/m², 3-20 through holes per cm², the holes having a diameter in CD and MD of 1-3 mm, and at least 70% by weight of the nonwoven ADL includes fibers having a fiber diameter of 12-22 µm.

18 Claims, 4 Drawing Sheets

(51) Int. Cl.
- *A61F 13/511* (2006.01)
- *A61F 13/537* (2006.01)
- *B32B 5/26* (2006.01)
- *B32B 5/02* (2006.01)
- *B32B 5/08* (2006.01)
- *B32B 3/26* (2006.01)
- *A61F 13/49* (2006.01)
- *A61F 13/512* (2006.01)
- *A61F 13/53* (2006.01)

(52) U.S. Cl.
CPC ........ *A61F 13/5121* (2013.01); *A61F 13/537* (2013.01); *B32B 3/266* (2013.01); *B32B 5/022* (2013.01); *B32B 5/08* (2013.01); *B32B 5/26* (2013.01); *A61F 2013/1556* (2013.01); *A61F 2013/15447* (2013.01); *A61F 2013/5127* (2013.01); *A61F 2013/530233* (2013.01); *A61F 2013/530299* (2013.01); *A61F 2013/530343* (2013.01); *A61F 2013/530481* (2013.01); *A61F 2013/53782* (2013.01); *B32B 2262/0253* (2013.01); *B32B 2262/0261* (2013.01); *B32B 2262/0276* (2013.01); *B32B 2262/062* (2013.01); *B32B 2262/067* (2013.01); *B32B 2262/14* (2013.01); *B32B 2307/718* (2013.01); *B32B 2307/726* (2013.01); *B32B 2307/728* (2013.01); *B32B 2307/7265* (2013.01); *B32B 2555/00* (2013.01)

(56) References Cited

U.S. PATENT DOCUMENTS

| | | | |
|---|---|---|---|
| 7,371,919 | B1 | 5/2008 | Busam et al. |
| 7,589,249 | B2 | 9/2009 | Gubernick et al. |
| 7,956,236 | B2 | 6/2011 | Ponomarenko et al. |
| 8,022,267 | B2 | 9/2011 | Hellström et al. |
| 2005/0049567 | A1 | 3/2005 | Cree et al. |
| 2005/0054999 | A1 | 3/2005 | Morman et al. |
| 2005/0267429 | A1 | 12/2005 | Cohen |
| 2008/0294138 | A1* | 11/2008 | Andersson ........ A61F 13/15203 604/385.23 |
| 2012/0136329 | A1 | 5/2012 | Carney |
| 2012/0209233 | A1 | 8/2012 | Steffen et al. |
| 2013/0022784 | A1* | 1/2013 | Uematsu ........... A61F 13/51104 428/138 |
| 2013/0158496 | A1 | 6/2013 | Seyler et al. |
| 2013/0261583 | A1 | 10/2013 | Hwang et al. |

OTHER PUBLICATIONS

Written Opinion (PCT/ISA/237) issued on Aug. 14, 2014, by the Swedish Patent Office as the International Searching Authority for International Application No. PCT/SE2013/051432.

International Preliminary Report on Patentability (PCT/IPEA/409) issued on Dec. 7, 2015, by the European Patent Office as the International Searching Authority for International Application No. PCT/SE2013/051432.

* cited by examiner

ABSORBENT ARTICLE HAVING ACQUISITION LAYER

TECHNICAL FIELD

The present invention pertains to an improved absorbent article comprising a nonwoven acquisition and distribution layer.

BACKGROUND ART

Absorbent articles for hygiene purposes are intended to absorb body liquids such as urine and blood. Users put high demands on such articles, requiring them to be thin and comfortable and at the same time to effectively absorb body liquids leaving the surface of the article dry.

Absorbent articles, such as sanitary napkins, diapers, incontinence guards and the like typically include a liquid pervious topsheet, intended to be facing the wearer during use, a liquid impervious backsheet and an absorbent structure there between. A liquid acquisition and distribution layer (ADL), in the form of a highloft nonwoven, is commonly incorporated and placed between the topsheet and the absorbent structure. An example of an absorbent article comprising an ADL in the form of a spunbond nonwoven is disclosed in US 20120209233 A1. The ADL should have the ability to receive and spread the liquid before it is absorbed by the absorbent structure.

Most ADL are able to receive and further distribute the liquid to the underlying absorbent structure, but are less effective in draining themselves and the liquid pervious topsheet of the liquid. The result is that liquid stays in topsheet and ADL leading to malodours.

SUMMARY

The object of the invention is to provide an improved absorbent article having an acquisition and distribution layer solving the above problem. This is achieved by the absorbent article as defined in claim 1.

The present invention relates to an absorbent article, the absorbent article comprising a liquid permeable top sheet, a liquid impermeable back sheet, and an absorbent core being arranged between the top sheet and the back sheet, and an acquisition and distribution layer of a nonwoven material being arranged between the top sheet and the absorbent core.

The acquisition and distribution layer (ADL) of the nonwoven material has a basis weight of 20-40 $g/m^2$, which may in one aspect be at least 20 $g/m^2$ and less than 30 $g/m^2$. The ADL has 3-20 through holes per $cm^2$, which may in one aspect be 3-15 through holes per $cm^2$. The holes have a diameter in CD and MD of 1-3 mm, which may in one aspect be 1.5-2.5 mm. At least 70% by weight the nonwoven material comprises fibres having a fibre diameter of 12-22 μm.

According to one embodiment at least 70% by weight of the nonwoven material comprises fibres having a fibre diameter of at least 15 and less than 19 μm.

According to another embodiment the open area of the nonwoven material may be 35-65%, and which may in one aspect be 40-60%.

According to a further aspect the through holes are funnel shaped.

According to a further embodiment the nonwoven material has a thickness of 0.8-1.2 mm at 0.5 kPa.

The ADL provides excellent drainage of captured fluid which leads to an increased dryness of both topsheet and ADL leading to an improved comfort and less malodours.

DETAILED DESCRIPTION

The absorbent article of the invention being a personal hygiene article may be any type of absorbent personal hygiene article. The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, panty liners and sanitary panties; diapers and pant diapers for infants and incontinent adults; incontinence pads; diaper inserts and the like.

The absorbent article comprises a liquid permeable topsheet, a liquid impermeable backsheet, and an absorbent core enclosed between the topsheet and the backsheet, and an acquisition and distribution layer arranged between the topsheet and the absorbent core.

The ADL is of a nonwoven material and may be substantially free from absorbing fibres and superabsorbent material. The nonwoven material of the ADL may comprise thermoplastic polymer fibres, and may be selected from but not limited to, polyesters, polyamides and polyolefins such as polyethylenes (PE) and polypropylenes (PP), and may be a mixture of any of these. The ADL may be of a spunbonded material and may be a spunbond-meltbond-spunbond (SMS) material. The non-woven material may be hydrophilic. A hydrophilic material may be obtained by adding a surfactant. A hydrophilic material facilitates liquid penetration and draining, thus maintaining free volume capacity for the next gush of liquid. The basis weight of the ADL is 20-40 $g/m^2$, and may be at least 20, but less than 30 $g/m^2$.

The ADL has 3-20 through holes per $cm^2$, which may be 3-15, and may be 3-10 through holes per $cm^2$. The holes have a diameter in cross direction (CD) and machine direction (MD) of 1-3 mm, which may be 1.5-2.5 mm. The holes may have any shape, such as a round or oval shape.

The through holes in the ADL may form protrusions that depend from the surface of the material. The protrusions may be funnel shaped and extend from the surface of the ADL and towards the absorbent core. The narrowest part of the funnel may be located closest to the core which may additionally prevent liquid from being transported in a direction towards the topsheet.

The thickness of the ADL may be 0.8-1.2 mm at 0.5 kPa as measured according to WSP120.6.R4(12).

The ADL may have an open area of 35-65%, and may be 40-60%.

At least 70% by weight of the nonwoven material comprises fibres having a fibre diameter of 12-22 μm, which may be at least 15 and less than 19 μm.

30% by weight or less of the nonwoven material may comprise fibres having a fibre diameter of less than 12 μm, which may be less than 15 μm. The lower part of the range may be more than 0.1 μm.

The fibres may have a round or non-round cross-section.

The ADL may be of an SMS material. An ADL of a spunbond-meltbond-spunbond (SMS) material may comprise 70-90% by weight of spunbonded fibres having a fibre diameter of 12-22 μm and 10-30% by weight of meltbonded fibres having a fibre diameter of 0.1 to 12 μm.

The topsheet and the backsheet of the absorbent article may extend together laterally outside of the absorbent core along the whole circumference of the absorbent core and be connected to each other in an edge joint around the periphery of the absorbent core. The edge joint may be formed in any suitable manner as known in the art such as by means of adhesive, ultrasonic bonding, thermo-bonding, stitching, etc.

The topsheet may consist of any material which is suitable for the purpose, i.e. be soft and liquid pervious, such as nonwoven materials. Laminates consisting of two or more materials, e.g. spunbond, meltblown, carded, hydroentangled, wetlaid nonwovens etc may be used. Suitable nonwoven materials can be composed of natural fibres, such as wood pulp or cotton fibres, manmade fibres, such as polyester, polyethylene, polypropylene, viscose etc., or from a mixture of natural and manmade fibres.

The topsheet may have a basis weight of 10-20 $g/m^2$. The average fibre diameter of a nonwoven topsheet material may be between 10-20 µm, such as 16 µm. The topsheet may be non-apertured.

The backsheet is fluid impermeable. However, backsheet materials that are only fluid repellant may be used particularly in instances where relatively small amounts of urine are expected to be taken up. The backsheet is commonly constituted by a thin, flexible, fluid-impermeable plastic film, but fluid-impermeable nonwoven materials, fluid impermeable foams and fluid impermeable laminates are also contemplated within the scope of the invention. The backsheet may preferably be breathable, implying that air and vapor may pass through the backsheet while still preventing liquids from passing through the backsheet material. Furthermore, the backsheet may have an outer, garment-facing surface of a textile material such as nonwoven, a thin plastic film, e.g. a polyethylene or polypropylene film, a nonwoven material coated with a liquid impervious material, a hydrophobic nonwoven material, which resists liquid penetration or laminates of plastic films and nonwoven materials.

The absorbent core may be made up of any suitable absorbent or fluid uptake material as known in the art, such as one or more layers of cellulose fluff pulp, foam, fibre waddings, etc. The absorbent core may contain fibres or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. An absorbent structure may comprise 40-80% superabsorbents and 60-20% pulp fibres. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as baby diapers, adult incontinence diapers and pads, pant diapers, panty liners, sanitary napkins etc.

BRIEF DESCRIPTION OF THE DRAWINGS

The invention will now be described by means of example referring to the figures. In this example of the invention the absorbent article is a urine incontinence protector in the form of a diaper 1. In FIG. 1, the absorbent article is seen from the side of the absorbent article that is intended to be facing towards a wearer's body when being worn, and in FIG. 2, it is seen in cross-section along the line II-II in FIG. 1. The drawing shows an embodiment of a diaper 1 for an infant or an incontinent adult, said diaper typically comprises a chassis comprising a liquid permeable topsheet 2, a liquid impermeable backsheet 3 and an absorbent body 4 enclosed there between. The liquid permeable topsheet 2 may consist of a nonwoven material. The liquid impermeable backsheet 3 may consist of a thin plastic film. The topsheet 2 and the backsheet material 3 may have a somewhat greater extension in the plane than the absorbent core 4 and extend outside the edges thereof. The layers 2 and 3 are connected to each other within the projecting portions thereof, e.g. by gluing or welding by heat or ultrasonic. The topsheet and/or the backsheet may further be attached to the absorbent core by any method known in the art, such as adhesive, heat bonding etc. The absorbent core may also be unattached to the topsheet and/or the backsheet.

The absorbent core 4 can be of any conventional kind. It may be a combination of cellulosic fluff pulp and superabsorbents in an absorbent body.

Figure 1:
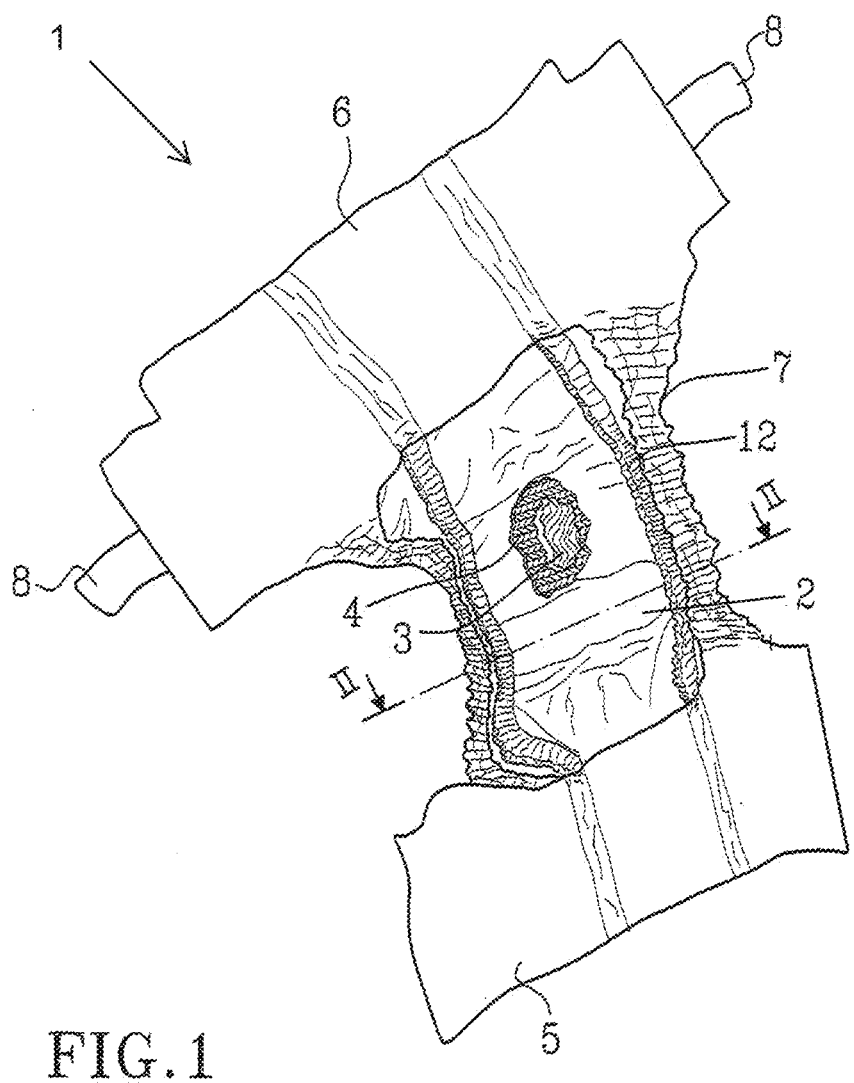
FIG. 1 shows an embodiment of an absorbent article according to the invention, seen from the side which will be facing the user when it is being worn.

The diaper 1 disclosed in FIG. 1 is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The back portion 6 is provided with a pair of adhesive tape tabs 8 or other type of attachment means such as hook-and-loop type fasteners.

The diaper 1 comprises elasticized side flaps 10 forming leg openings. Elastification is provided by elastic members 11 secured between the topsheet and backsheet in the side flap region 10. The diaper disclosed in FIGS. 1 and 2 further comprises elastic barrier flaps 12 having a proximal edge 13 and a distal edge 14 and elastic member 15 spacing the distal edge 14 away from the topsheet. These barrier flaps 12 form leakage barriers and are at their proximal edges 13 secured to the topsheet 2 close to the lateral edges of the absorbent core 4 either in the area of the side flaps 10 or above the absorbent core 4.

The diaper may further comprise an elasticized waist in the form of elastic members extending in the transverse direction of the article in the waist portion thereof.

It is however understood that the diaper described above and shown in the drawing only represents one non-limiting example and that the present invention is not limited thereto, but can be used in any type of absorbent articles as defined above.

A fluid receiving layer 16 in the form of a nonwoven ADL is located between the absorbent core 4 and the topsheet 2. During use of the article the ADL is intended to be located in the crotch area of the diaper 1. The ADL is a nonwoven material having a basis weight of 20-40 g/m² and having 3-20 through holes per cm², the holes having a diameter in CD and MD of 1-3 mm. The through holes are not shown in FIG. 2. The ADL may be of an SMS material having a surface weight of 25 g/m² divided up as 10/5/10 g/m². The ADL 16 is a three-dimensional layer having through holes 20 that originate in a first surface 21 and extend towards a second surface 22 as shown in FIG. 3. The distance between the first surface 21 and the second surface 22 is the apparent thickness of the layer 16. When fluid 23 reaches the first surface 21 of the ADL 16, it spread on the surface 21 before passing through the apertures 20 as shown in FIG. 3. The through holes 20 form protrusions 19 in the ADL 16. The protrusions 19 may extend from the surface towards the topsheet 2 or, as shown in FIG. 3, towards the absorbent core 4.

Figure 2:
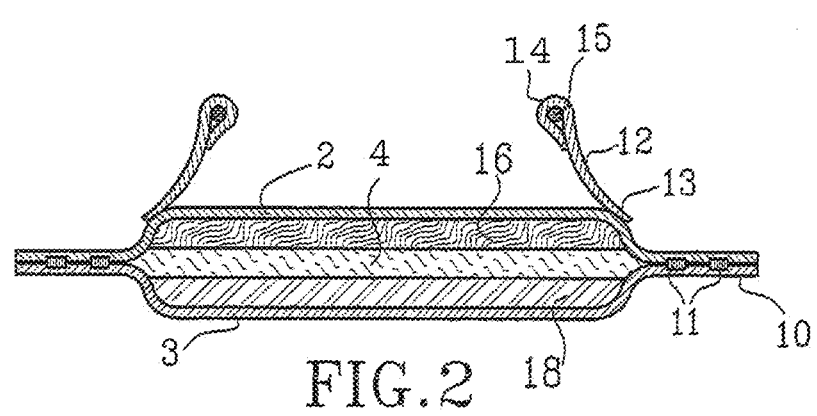
FIG. 2 shows a cross-sectional view of the absorbent article of FIG. 1, along the line II-II (holes in ADL not shown).
Figure 3:
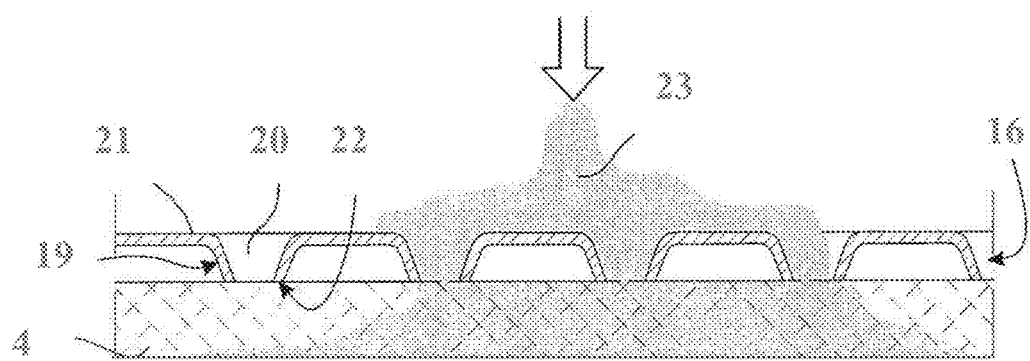
FIG. 3 is a cross-sectional view of an embodiment of an ADL according to the invention and a core layer.

The absorbent core 4 may have one or more 4, 18 absorbent layers extending over the front, crotch and rear regions of the diaper, see FIG. 2. The material used in the storage layers should have the ability to absorb and store large quantities of fluid and may comprise 40-80% super-absorbents and 60-20% pulp fibres.

Test Methods

Surface Dryness

The following test was used to determine the amount of liquid left in a material after subjection to a certain amount of fluid. It gives a good indication of surface dryness and the result is reported as "not drained fluid" (g/m²). The test liquid used was 0.9% NaCl.

Circular entities having a diameter of 6 cm are punched out of the materials to be tested. The weights of the test samples are noted prior to testing.

Figure 4:
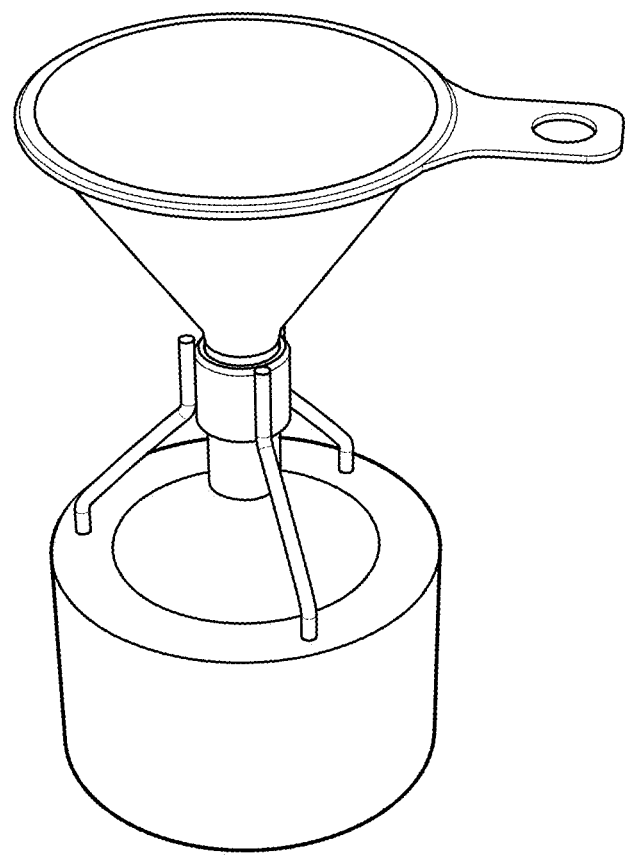
FIG. 4 is a drawing of the funnel used in the test herein for measuring surface dryness.

A funnel connected to a cylinder, see FIG. 4, is placed on top of the material to be tested which material in turn is placed on seven filter papers (140×140 mm). When placing the materials below the cylinder it is crucial that there is no gap between the material and the cylinder wall. 15 ml of test fluid is added to the funnel with a finger placed at the outlet of a measuring cylinder in order to have a constant and controlled flow of the liquid into the cylinder. A timer is started to time 1 minute when all liquid has been added to the test material. After 1 minute the tested material is removed from the filter papers as an entity with a tweezers and weighed separately if more than one material was tested. The weight of the test sample is thus noted prior to the start of the test and after the 1 minute draining. The difference between the weight before and after the test is the "not drained fluid" (in g/m²) left in the material. The different ADL materials were tested alone as first layers (No 1, 3, 5, 7, 9, 11) and then as second layers together with a 17 gsm, PP nonwoven spunbonded, 1.8 den, topsheet (No 2, 4, 6, 8, 10, 12), see Table 1 below.

TABLE 1

Tested ADL materials

| No | First Layer (1st layer) | Second layer (2nd layer) |
|---|---|---|
| 1 | Highloft A (50 gsm): 9 den PET Hollow Spiral Crimp + bico PP/PET + bico CoPET/PET fibres | — |
| 2 | Topsheet | Highloft A |
| 3 | Highloft B (50 gsm): 12 den PET Hollow fibers + 6 den PET/PET binder fibers + 3 den PET/PP welding fibers | — |
| 4 | Topsheet | Highloft B |
| 5 | Highloft C (50 gsm): 70% PET and 30% PP fibres | — |
| 6 | Topsheet | Highloft C |
| 7 | Highloft D (40 gsm): 100% bico PP/PE fibres | — |
| 8 | Topsheet | Highloft D |
| 9 | Nonwoven apertured (70 gsm): Philic SMS 100% PP fibres, open area 17% | — |
| 10 | Topsheet | NW apertured |
| 11 | Embodiment of the invention (25 gsm): 100% spunbonded PP fibres, average fibre diameter 18.5 µm, material thickness 1 mm, 5 holes/cm² having CD/MD 2 mm | — |
| 12 | Topsheet | Embodiment of the invention (25 gsm) |

The highlofts A-D are carded air through bonded materials (ATB). The topsheet used in the test is in all cases a 17 gsm, PP nonwoven spunbonded, 1.8 den.

Figure 5:
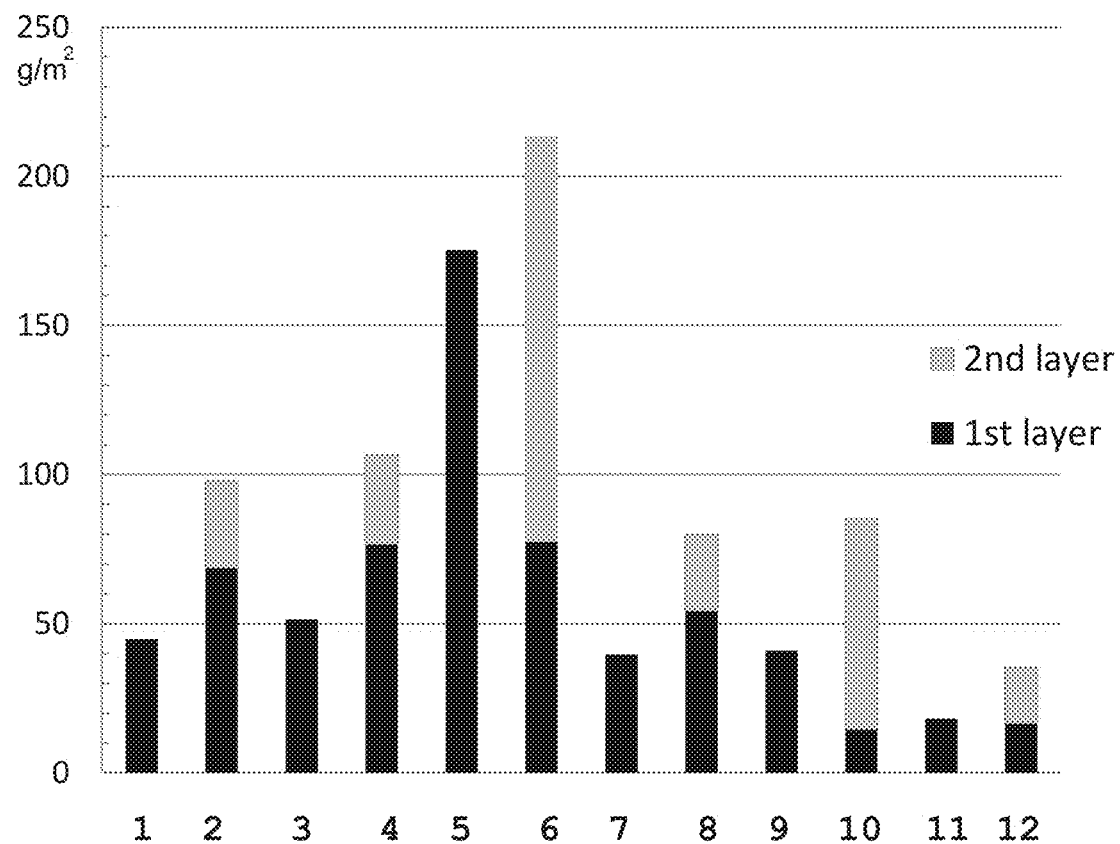
FIG. 5 is a graph showing amount of fluid (in $g/m^2$) remaining in different types of ADL and ADL combined with a topsheet, as measured according to the surface dryness test disclosed herein.

The results of the surface dryness test for the above materials are shown in FIG. 5 showing the "not drained fluid" in g/m² for the tested materials. The sample material according to an embodiment of the invention (No 11 and 12) was superior to the other tested materials both compared with different types of highlofts and apertured material. The inventive material drained effectively both itself and the nearby topsheet of liquid. This is seen in FIG. 5 as only small amounts not drained fluid stayed in the topsheet and ADL for No 11 and 12. This is an extremely important property of an ADL material as liquid left in topsheet and ADL will lead to malodours and discomfort. Excellent results have also been achieved with an ADL according to an embodiment of the invention wherein the ADL is of an SMS material (10/5/10 g/m²).

Thickness Measurement

The thicknesses of the materials were measured according to a standard test method for nonwoven materials: WSP120.6.R4(12). Specifically, 4.1 for normal nonwovens were used and 7.2 Option A for normal nonwovens using a uniform pressure of 0.5 kPa.

Open Area and Hole Diameter Measurement

The following method may be used to determine the open area and the hole diameter for an apertured material.

Apparatus:
a Nikon microscope
a personal computer
software NIS-Elements BR 3.10

Procedure:
collect a sample of the apertured material
position the sample on the reading surface of the microscope
start the software
catch a representative image of the sample
perform the analysis of the properties by contrast technique involving highlighting of the areas occupied by the holes.

The software calculates the diameters of the highlighted holes as major diagonal and minor diagonal of a rhombus inscribed in the hole. The ratio between the diameters is used to determine the actual average conformation of the holes to a circular shape, wherein a ratio of 1 implies a perfectly circular shape.

The average hole area value obtained by means of the software is used to calculate the percent open area.

Alternative methods for determining open area and hole diameter may be used, such as manual methods and methods based on scanning electron microscopy.

Measurements of Fibre Diameter

Methods for measuring the fibre diameter of a nonwoven material are known to the skilled man in the art. In the present case the fibre diameter were obtained by computerized measurements of pictures of the nonwoven material taken by an Environmental Scanning Electron Microscope XL 30-TMP from FEI Company. It is assumed that the fibre width is equal to the fibre diameter for both round and non-round fibres.

The invention claimed is:

1. An absorbent article comprising a liquid permeable top sheet, a liquid impermeable back sheet, an absorbent core being arranged between the top sheet and the back sheet, and an acquisition and distribution layer of a nonwoven material being arranged between the top sheet and the absorbent core, wherein the acquisition and distribution layer includes a longitudinal center-line extending in a direction from a front portion of the absorbent article to a rear portion of the absorbent article, and the liquid permeable top sheet covers the longitudinal center-line of the acquisition and distribution layer, and wherein said nonwoven material has a basis weight of 20-40 g/m$^2$, 3-20 through holes per cm$^2$, the holes having a diameter in CD and MD of 1-3 mm, and at least 70% by weight of the nonwoven material comprises fibres having a fibre diameter of 12-22 μm.

2. The absorbent article according to claim 1, wherein at least 70% by weight the nonwoven material comprises fibres having a fibre diameter of at least 15 and less than 19 μm.

3. The absorbent article according to claim 1, wherein 30% by weight or less of the nonwoven material comprises fibres having a fibre diameter of less than 12 μm.

4. The absorbent article according to claim 1, wherein the nonwoven material has a basis weight of at least 20 g/m$^2$ and less than 30 g/m$^2$.

5. The absorbent article according to claim 1, wherein the nonwoven material has a thickness of 0.8-1.2 mm at 0.5 kPa.

6. The absorbent article according to claim 1, wherein the open area of the nonwoven material is 35-65%.

7. The absorbent article according to claim 1, wherein the nonwoven material has 3-15 through holes per cm$^2$.

8. The absorbent article according to claim 1, wherein the holes have a diameter in CD and MD of 1.5-2.5 mm.

9. The absorbent article according to claim 1, wherein the through holes are funnel shaped.

10. The absorbent article according to claim 1, wherein the nonwoven material is a spunbonded nonwoven material.

11. The absorbent article according to claim 1, wherein the nonwoven material is a spunbond-meltblown-spunbond (SMS) material.

12. The absorbent article according to claim 11, wherein the spunbond-meltblown-spunbond (SMS) material comprises fibres having a diameter of 0.1 to 12 μm.

13. The absorbent article according to claim 1, wherein the top sheet is of a nonwoven material.

14. The absorbent article according to claim 1, wherein the top sheet is of a non-apertured nonwoven material.

15. The absorbent article according to claim 1, wherein the top sheet has a basis weight of 10-20 g/m$^2$.

16. The absorbent article according to claim 1, wherein the top sheet is of a spunbonded nonwoven material.

17. The absorbent article according to claim 1, wherein the liquid permeable top sheet covers a portion of the acquisition and distribution layer having 3-20 through holes per cm$^2$.

18. The absorbent article according to claim 1, wherein a surface of the top sheet covers an entirety of a surface of the acquisition and distribution layer which faces away from the absorbent core.

* * * * *